United States Patent [19]

Schickling et al.

[11] Patent Number: 5,127,900
[45] Date of Patent: Jul. 7, 1992

[54] CARDIOTOMY RESERVOIR

[75] Inventors: David Schickling, Laguna Beach; Jeanne Pierson, Irvine, both of Calif.

[73] Assignee: Medtronic Inc., Minneapolis, Minn.

[21] Appl. No.: 452,964

[22] Filed: Dec. 19, 1989

[51] Int. Cl.⁵ .......................................... A61M 37/00
[52] U.S. Cl. ...................................... 604/4; 604/403; 128/DIG. 3; 210/436
[58] Field of Search ............... 128/DIG. 3; 604/4-7, 604/403; 210/436, 437, 438, 439, 457, 458

[56] References Cited

U.S. PATENT DOCUMENTS

| | | | |
|---|---|---|---|
| 3,507,395 | 4/1970 | Bentley | 210/443 |
| 3,768,653 | 10/1973 | Brumfield | 210/188 |
| 3,891,416 | 6/1975 | Leonard et al. | 55/178 |
| 3,993,461 | 11/1976 | Leonard et al. | 55/178 |
| 4,157,965 | 6/1979 | Raible | 210/305 |
| 4,208,193 | 6/1980 | Munsch et al. | 55/36 |
| 4,243,531 | 1/1981 | Crockett et al. | 210/188 |
| 4,282,180 | 8/1981 | Raible | 422/46 |
| 4,568,367 | 2/1986 | Gremel et al. | 55/178 |
| 4,676,771 | 6/1987 | Henke | 604/4 |
| 4,705,497 | 11/1987 | Shitaokoshi et al. | 604/4 |
| 4,737,139 | 8/1988 | Zupkas et al. | 604/4 |
| 4,743,371 | 5/1988 | Servas et al. | 210/188 |

Primary Examiner—Robert A. Hafer
Assistant Examiner—Kerry Owens

[57] ABSTRACT

A cardiotomy reservoir which employs an inner wall structure which defines a central receiving chamber. The receiving chamber wall is tapered inwardly to provide a smooth blood flow along an arcuate imperforate portion which extends from the top to the bottom thereof into the blood receiving chamber. Apertures in another arcuate portion of the wall member allow fluid communication between the receiving chamber and the blood treatment element. Blood flow directing means direct blood entering the inlet port of the device downward toward the bottom of the receiving chamber along the imperforate portion of the inner wall so that the inflowing blood does not splash and has low turbulence.

12 Claims, 2 Drawing Sheets

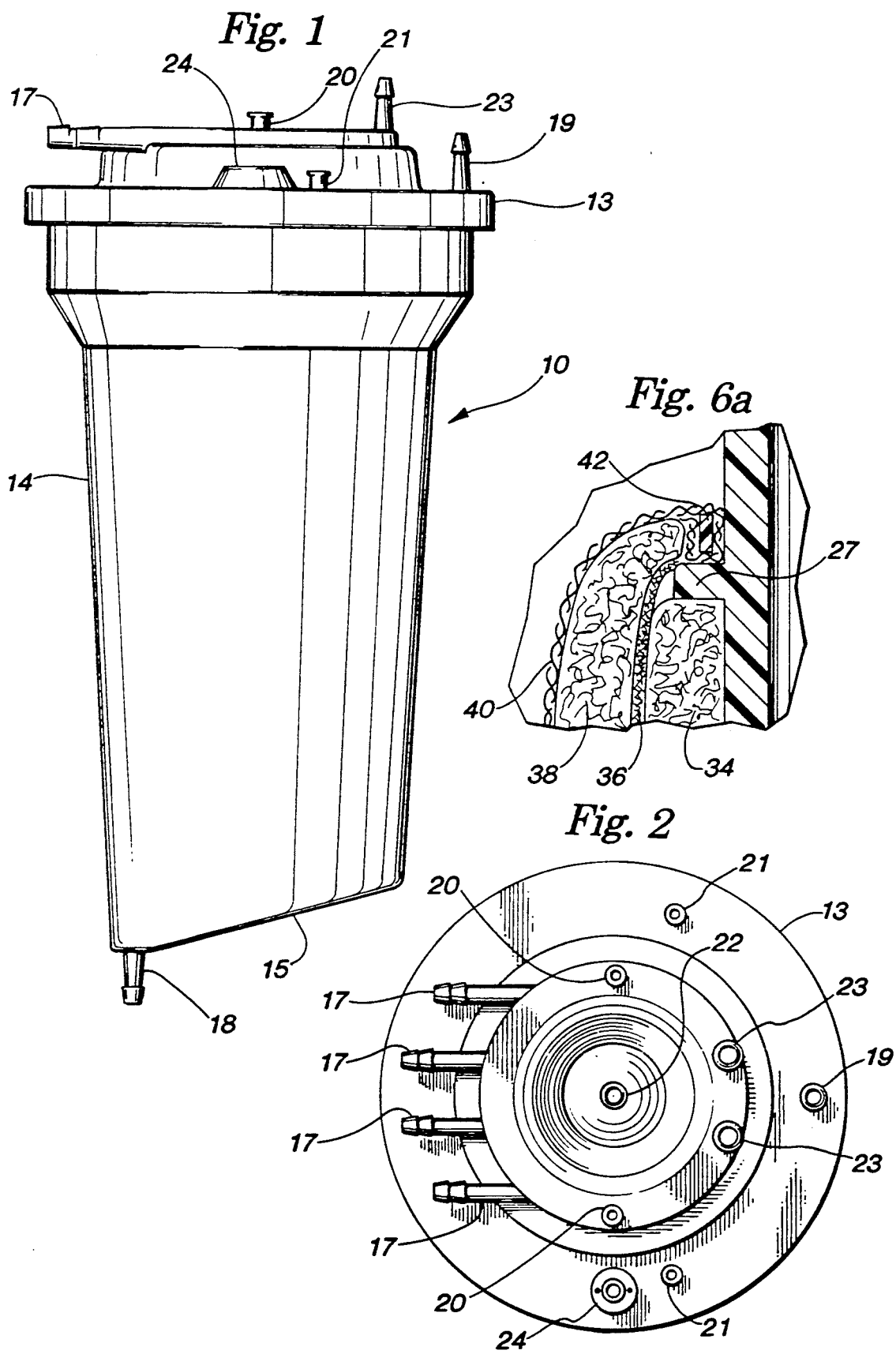

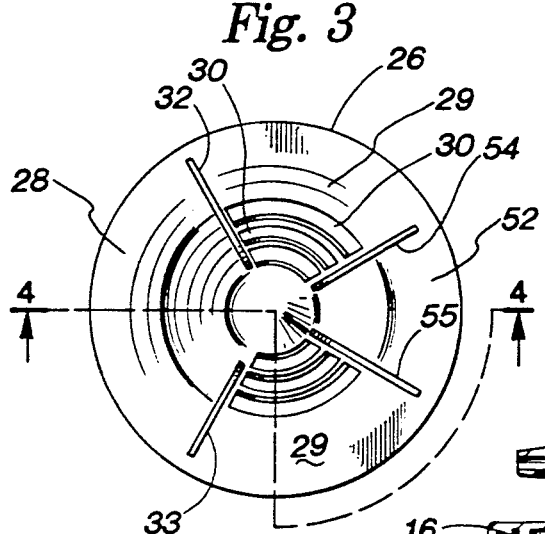
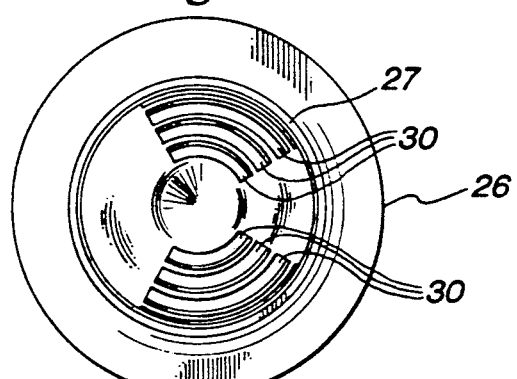
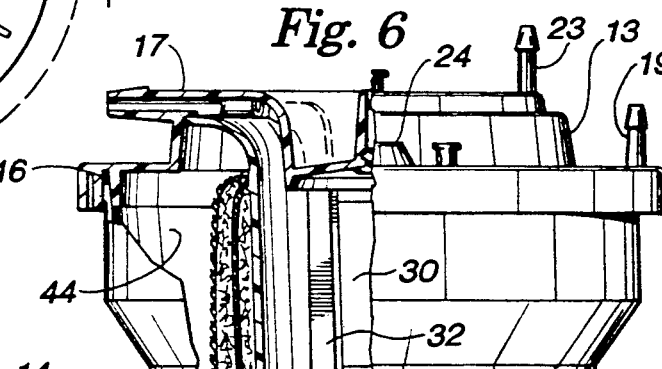
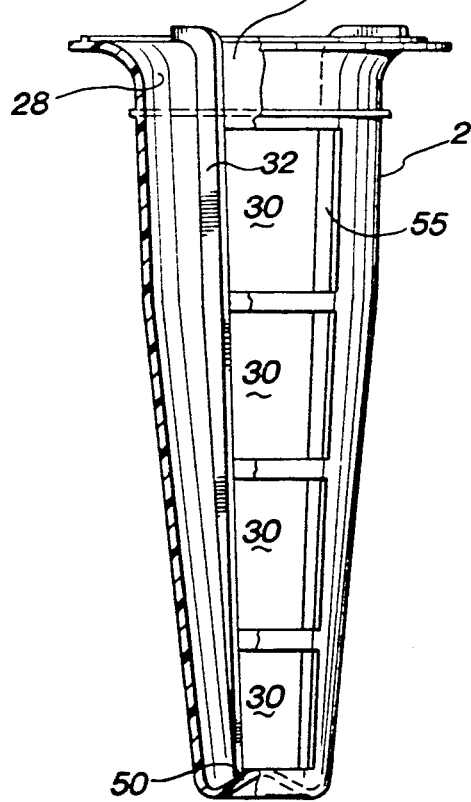

CARDIOTOMY RESERVOIR

FIELD OF THE INVENTION

The present invention pertains to cardiotomy reservoir structures. Cardiotomy reservoirs are currently used in major surgical procedures, such as open heart surgery, for receiving blood from a cardiotomy sucker and other sources, defoaming the blood, filtering out debris and returning it to the patient.

DESCRIPTION OF PRIOR ART

U.S. Pat. No. 3,507,395 discloses a cardiotomy reservoir which includes a plate in the path of incoming blood for spreading the blood into a thin sheet before it is passed through filter material. The thin sheet of blood facilitates removal of air bubbles therefrom.

In U.S. Pat. No. 3,768,653 there is disclosed a filtering cardiotomy reservoir which discharges blood into a device in a flat stream tangentially against a tubular sidewall of the device in a manner said to cause deposition of surgical debris on the sidewall.

In U.S. Pat. Nos. 3,891,416 and 3,993,461 there are disclosed cardiotomy reservoirs said to be improvements over that of U.S. Pat. No. 3,507,395. Blood entering from a bottom inlet flows into a central receiving chamber from which it passes to a cylindrical filter through perforations in the chamber wall. Blood may also enter the receiving chamber from the top of the device through a resupply port. No provision is made to prevent splashing or turbulence as a result of the blood entering from the top.

In U.S. Pat. No. 4,157,965 there is described another cardiotomy reservoir in which blood entering from the top of the device falls onto the apex of an upwardly extending cone, flowing downward and outward in a sheet-like manner from the apex toward a filter means. This structure is said to reduce the formation of air emboli and to reduce blood cell damage which results from splashing and turbulence.

In U.S. Pat. No. 4,208,193 there is described a cardiotomy reservoir in which blood entering at the top of the device is passed immediately into a central chamber filled with a defoaming sponge material. The blood flows outwardly from the central chamber through perforations in the chamber wall and then through additional filter and defoaming elements. A similar device is shown in U.S. Pat. No. 4,243,531.

In U.S. Pat. No. 4,737,139 there is described a reservoir in which blood from surgical and venous sites are separately treated and then combined. The cardiotomy blood enters at the top of the device and flows through a funnel onto the apex of an upward pointing cone and then downwardly and outwardly along the outside of the cone toward a surrounding defoaming and filtering element. Four vertically extending flow directing fins quarter the upper portion of the inverted cone.

Additional cardiotomy reservoir structures are described in the background sections of the above mentioned patents and in U.S. Pat. Nos 4,705,497, 4,568,367 and 4,743,371.

SUMMARY OF THE INVENTION

The present invention is a cardiotomy reservoir which is distinguished by a novel structure which provides for a smooth blood flow with low turbulence into the device in a manner different from that disclosed or suggested in the prior art.

The cardiotomy reservoir of the invention employs a novel inner wall member which supports a blood treatment means on the outside thereof. The inner wall member is tapered inwardly to provide a smooth blood flow along an imperforate arcuate portion which extends from the top to the bottom thereof into a blood receiving chamber defined by the wall member. Apertures in another portion of the wall member allow fluid communication between the receiving chamber and the blood treatment means. Blood flow directing means direct blood entering the inlet port of the device downward toward the bottom of the receiving chamber along the arcuate imperforate portion of the inner wall so that the inflowing blood does not splash and has low turbulence.

BRIEF DESCRIPTION OF THE DRAWINGS

FIG. 1 is a side elevational view of the preferred device of the invention.

FIG. 2 is a top plan view of the device of FIG. 1.

FIG. 3 is a top plan view of the inner receiving chamber wall member.

FIG. 4 is a view taken at line 4—4 of FIG. 3.

FIG. 5 is a bottom plan view of the subject FIGS. 3 and 4.

FIG. 6 is a side elevational view of the device of the invention with parts cut away to show the interior assembly thereof.

FIG. 6a is a greatly enlarged fragmentary detail view of a part of FIG. 6.

DETAILED DESCRIPTION OF THE PREFERRED EMBODIMENT

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

The cardiotomy reservoir of this invention comprises a rigid exterior housing generally designated by the numeral 10. The specific shape of the housing is not critical, but it is preferably a generally cylindrical structure as shown in the FIGS. 1 and 6. Suitably the housing is made of a rigid moldable plastic material such as polycarbonate, polyacrylate or polyester thermoplastic which is preferably clear to enable observation of blood levels within the device. Suitable plastics are the polycarbonate resins sold by General Electric Co. under the LEXAN trademark and by Mobay Corporation under the MAKROLON trademark.

Housing 10 comprises a top 13, generally cylindrical sidewall 14 and a bottom 15 integrally molded with sidewall 14. Desirably the sidewall 14 is tapered inwardly from top to bottom to assure drainage. The top 13 is suitably a separately formed cover member. A circumferential gasket 16 provides a fluid tight seal between the top 13 and the upper edge of sidewall 14. Alternatively the top 13 may be sealingly bonded to the sidewall 14 by adhesive, heat or ultrasonic bonding techniques. Fluid communication into and out of the device is provided by at least one cardiotomy inlet port 17 at the top of the device and an outlet port 18 in the bottom portion thereof. Generally it is desired that a plurality of cardiotomy inlet ports 17 be provided so that blood may be received from several locations at the surgical site.

Also located at the top of housing 10 is a vent port 19. Optionally the device is further provided with luer ports 20 and 21 for introducing medicines or the like, a quick priming port 22 and one or more chest drainage ports 23. A dual action pressure release valve 24 may be included to assure that the internal pressure of the device stays within predetermined values.

Normally all the parts in the device will be covered by removable caps, not shown, until the port is to be accessed.

Located within the housing 10 is an inner wall member 26 which defines a central blood receiving chamber within the device. Receiving chamber wall member 26 has a generally conical or horn-like shape which slopes downwardly and inwardly from the top to a closed bottom. Wall member 26 includes a first arcuate portion 28 which provides a continuous imperforate surface from just below the inlet port opening to the bottom of the device so that cardiotomy blood entering the device will flow smoothly into the receiving chamber along the surface of portion 28 without splashing and with minimal turbulence. Another arcuate portion 29 of member 26 includes at least one aperture or window 30 to allow blood to exit the receiving chamber. Vanes 32 and 33 separate imperforate arcuate wall portion 28 from the windowed portion 29 and provide blood direction means for directing blood entering the housing onto the imperforate arcuate portion 28 as the blood flows into the receiving chamber.

Surrounding the outside of the receiving chamber wall 26 is a blood treatment means which comprises at least a blood defoaming element. Preferably the blood treatment means comprises a first defoaming element 34, a depth filter element 36, a second defoaming element 38 and a sock like element 40. The sock-like element 40 is a mesh or knit fabric which holds the defoaming and filtering elements in place against the outside of wall member 26. Suitably the sock-like element is held in place by means of a tiestrap 42 surrounding the top of the sock and engaging receiving chamber wall member 26 above a ridge 27 which extends circumferentially around the outside of the receiving chamber wall above the highest windows 30.

Defoaming elements 34 and 38 are preferably formed of a thermally reticulated polyurethane foam. Typically defoaming elements 34 and 38 will have an average pore size of about 20 pores per inch. Desirably both are coated with a suitable defoaming agent. The depth filter element may be a 20 micron felt filter.

Between the sock 40 and the inner surface 44 of sidewall 14 is a space which provides a collection chamber for treated blood. Outlet port 18 opens into the bottom of this collection chamber.

Suitably the bottom 15 of the housing is tapered downwardly toward outlet port 18 to facilitate drainage from the blood receiving chamber to the outlet port. Desirably a central portion 46, shown in phantom in FIG. 6, of bottom 15 is indented and includes a central hump 48 which serves as a location means for the bottom of receiving chamber wall member 26. Structures 46 and 48 reduce volume at the bottom of the blood reservoir and, therefore, further facilitate drainage toward the exit port.

A corresponding hump 50 in the bottom of receiving chamber wall 26 mates with bottom hump 48 of the housing to provide positive location of the receiving chamber wall. Hump 50 also reduces dead volume at the bottom of the blood receiving chamber below the lowest window 30.

If the inventive device is intended to be used solely in surgical operations, windowed portion 29 of the receiving chamber wall 26 may encompass the entire arcuate surface of wall 26 on the outside of vanes 32 and 33. However, in the preferred structure shown in the figures, wall member 26 also includes a second imperforate arcuate portion 52 extending from the top to the bottom of the receiving chamber wall. Second imperforate portion 52 is disposed below the chest drainage ports 23. A second set of vanes, 54 and 55, direct blood received from the chest drainage ports down along the imperforate portion 52 as blood flows into the central receiving chamber. This structure allows the device to continue to be used after surgery for treating blood which is collected from a chest drain and returned to the body. Suitably portion 52 is disposed opposite portion 28 so that wall member 26 includes two apertured portions 29 between the respective sets of vanes 32, 54 and 33, 55. Imperforate portion 52 may comprise a smaller arcuate portion of wall 26 than portion 28 since the chest drainage tubes will usually be fewer in number and provide a lower blood flow rate than the cardiotomy blood inlet ports.

In operation blood from a surgical site is fed into the cardiotomy inlet ports 17 and is directed in a sheet-like flow along imperforate portion 24 of receiving chamber wall 26 into the central receiving chamber of the device. The blood then passes via apertures 30 through the respective defoaming and filtering elements 34, 36, 38 and 40 into the treated blood collection chamber from which it exits via outlet port 18. The blood may then be fed back into the body, usually after having been further oxygenated and/or cooled.

After surgery the cardiotomy ports 17 are sealed by cutting and clamping the connecting tubing or by removing the connecting tubing and recapping the ports 17. If the patient requires chest drainage, the open end of a drain tube sewn into the patient may be connected to a chest drainage port 23 so that the drainage may be filtered and returned to the patient. The return may be accomplished with an I.V. pump programmed to match the rate of bleeding or by periodic gravity drainage into the patient in a batch process. The cardiotomy ports and chest drainage ports are desirably separately provided in the device since the connecting tubing for the two functions conventionally have differently sized connecting ports. If medicines or the like are desired to be added to the blood they may be added in the receiving chamber via luer ports 20 or in the treated blood collection chamber via luer ports 21.

This completes the description of the preferred and alternate embodiments of the invention. Those skilled in the art may recognize other equivalents to the specific embodiment described herein which equivalents are intended to be encompassed by the claims attached hereto.

What is claimed is:

1. A blood reservoir device comprising
  a housing having top and bottom portions,
  at least one blood inlet port in the top portion of the housing for feeding blood into the interior of the housing,
  a blood outlet part in the bottom portion of the housing, bood treatment means including blood defoaming means, a blood collection chamber between an inner wall of the housing and the blood treating means for collecting treated blood, said collection chamber communicating with the outlet port and constructed to facilitate blood drainage through the outlet port, a blood receiving chamber extending within the housing below the inlet port, the chamber defined by a wall having a first portion with at least one aperture and a second portion with a) at least one downwardly and inwardly tapered continuous imperforate surface from the inlet port to the bottom and b) first blood flow direction means on said tapered surface, whereby the blood receiving chamber wall both directs blood from the inlet port to the treatment means and supports the treatment means within the housing.

2. A device as in claim 1 wherein the first blood flow direction means comprises a pair of inwardly projecting vanes extending from the top to the bottom of the receiving chamber wall, said vanes defining a space therebetween comprising said second portion of the receiving chamber wall.

3. A device as in claim 1 wherein the said receiving chamber wall member has a truncated, downwardly pointing, generally conical shape, said first portion of said receiving chamber wall comprising a first arcuate section of said truncated cone and said second portion of said receiving chamber wall comprising a second arcuate section of said truncated cone.

4. A device as in claim 3 wherein the said first arcuate section includes a plurality of apertures therethrough, said apertures distributed over the surface thereof from near the top to near the bottom thereof.

5. A device as in claim 1 wherein the housing includes a plurality of said cardiotomy blood inlet ports each of which is adapted to distribute blood onto the second portion of said receiving chamber wall.

6. A device as in claim 4 wherein said housing includes at least one wound drainage inlet port in the top portion of the housing for feeding drainage from a surgical wound into the blood receiving chamber within the housing, and said receiving chamber wall includes a third arcuate section providing a continuous imperforate surface from said wound drainage port to the bottom of the receiving chamber and second blood flow direction means for directing blood from said wound drainage port along said third arcuate section toward the bottom of said receiving chamber.

7. A device as in claim 6 wherein the receiving chamber wall further comprises a fourth arcuate portion having a plurality of apertures therethrough, the apertures in said fourth arcuate portion distributed from near the top to near the bottom of said fourth arcuate portion.

8. A device as in claim 7 wherein said first and second blood flow direction means comprise, respectively, first and second pairs of inwardly projecting vanes extending from near the top to near the bottom of the receiving chamber wall member.

9. A device as in claim 7 wherein the bottom portion of the housing comprises a locating indentation, and the bottom portion of the receiving chamber wall is closed and comprises a hump therein which engages the locating indentation in the bottom portion of the housing.

10. A device as in claim 1 wherein said blood treatment means further comprises a depth filter element.

11. A device as in claim 1 wherein said blood treatment means comprises a first defoaming element immediately adjacent the receiving chamber wall member, a depth filter element surrounding said first defoaming element and a second defoaming element surrounding said depth filter element.

12. A device as in claim 11 wherein the defoaming elements have an average pore size of about 20 pores per inch and said depth filter element is a felt filter having an average pore size of about 20 microns.

* * * * *